US010350257B2

(12) United States Patent
Park et al.

(10) Patent No.: US 10,350,257 B2
(45) Date of Patent: Jul. 16, 2019

(54) PHARMACEUTICAL COMPOSITION CONTAINING COMPLEX EXTRACT OF *CRATAEGI FRUCTUS* AND *CITRI PERICARPIUM* AS AN ACTIVE INGREDIENT FOR TREATING OR PREVENTING OBESITY OR LIPID-RELATED METABOLIC DISEASES

(71) Applicant: NEUMED, Seoul (KR)

(72) Inventors: Juyeon Park, Gyeonggi-do (KR); Dong Wook Lim, Seoul (KR); Mikyung Song, Seoul (KR)

(73) Assignee: NEUMED, Seoul (KR)

( * ) Notice: Subject to any disclaimer, the term of this patent is extended or adjusted under 35 U.S.C. 154(b) by 224 days.

(21) Appl. No.: 14/424,991

(22) PCT Filed: Jun. 21, 2013

(86) PCT No.: PCT/KR2013/005482
§ 371 (c)(1),
(2) Date: Feb. 27, 2015

(87) PCT Pub. No.: WO2014/035035
PCT Pub. Date: Mar. 6, 2014

(65) Prior Publication Data
US 2015/0202244 A1    Jul. 23, 2015

(30) Foreign Application Priority Data
Aug. 28, 2012  (KR) .................. 10-2012-0094213

(51) Int. Cl.
*A61K 36/752* (2006.01)
*A61K 36/734* (2006.01)
*A23L 33/105* (2016.01)

(52) U.S. Cl.
CPC .......... *A61K 36/752* (2013.01); *A23L 33/105* (2016.08); *A61K 36/734* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2004/0132816 A1 | 7/2004 | Liao et al. | 514/557 |
| 2007/0059386 A1* | 3/2007 | Lee | A61K 36/00 424/725 |
| 2010/0055213 A1 | 3/2010 | Kim et al. | 424/728 |
| 2010/0316741 A1 | 12/2010 | Kim et al. | 424/728 |

FOREIGN PATENT DOCUMENTS

| | | |
|---|---|---|
| KR | 10-2002-0080518 | 1/2003 |
| KR | 10-2002-0083763 | 1/2003 |
| KR | 10-2006-0010603 | 5/2006 |
| KR | 10-2006-0050066 | 12/2007 |
| KR | 10-2006-0113784 | 12/2007 |
| KR | 10-2003-0051995 | 6/2011 |
| WO | WO 2008119130 A1 * | 10/2008 ........... A61K 36/232 |

OTHER PUBLICATIONS

Kang et al. (2012) Biol. Pharm. Bull. 35(2): 223-230.*
Raskin et al. (2004) Current Pharmaceutical Design, 10, 3419-3429.*
Revilla et al. (1998) J. Agric. Food Chem. 46, 4592-4597.*
Yang et al. (2008) Innumopharmacology and Immunotoxicology, 30: 783-791.*
Letter/Written Diclosure of the Information Diclosure Statement provided herewith, mailed on Oct. 12, 2015, 2 pages.
Machine-generated English Language translation of Korean Patent Publication No. KR 10-2003-0005129, Korean Intellectual Property Office, 8 pages.
Partial English Language translation of relevant portions of Korean Patent Publication No. KR 10-2003-0005129, 1 page.
Machine-generated English Language translation of Korean Patent Publication No. KR 10-2003-0008184, Korean Intellectual Property Office, 8 pages.
Partial English Language translation of relevant portions of Korean Patent Publication No. KR 10-2003-0008184, 1 page.
Machine-generated English Language translation of Korean Patent No. KR 10-1043145, Korean Intellectual Property Office, 10 pages.
Partial English Language translation of relevant portions of Korean Patent No. KR 10-1043145, 2 pages.
Machine-generated English Language translation of of Korean Patent No. KR 10-0577674, Korean Intellectual Property Office, 13 pages.
Partial English Language translation of relevant portions of Korean Patent No. KR 10-0577674, 1 page.
Machine-generated English Language translation of Korean Patent No. KR 10-0787175, Korean Intellectual Property Office, 17 pages.
Partial English Language translation of relevant portions of Korean Patent No. KR 10-0787175, 4 pages.
Machine-generated English Language translation of Korean Patent No. KR 10-0786122, Korean Intellectual Property Office, 11 pages.
Partial English Language translation of relevant portions of Korean Patent No. KR 10-0786122, 2 pages.
International Search Report and Written Opinion, dated Sep. 27, 2013, in connection with International Patent Application No. PCT/KR2013/005482 [English Translation], 7 pages.
International Preliminary Report on Patentability, dated Mar. 10, 2015, in connection with International Patent Application No. PCT/KR2013/005482 [English Translation], 6 pages.
U.S. Appl. No. 12/518,010, filed Jun. 5, 2009, 2010/0316741, Dec. 16, 2010.
U.S. Appl. No. 14/785,312, filed Oct. 16, 2015.
U.S. Appl. No. 14/897,617, filed Dec. 10, 2015.
Letter/Written Opinion of the Information Disclosure Statement for the above-referenced application, mailed on Mar. 22, 2016, 2 pages.
Lee et al., "A Herbal Formula HT048, *Citrus unshiu* and *Crataegus pinnatifida*, prevents obesity by inhibiting adipogenesis and lipogenesis in 3T3-L1 preadipocytes and HFD-induced obese rats," Molecules 20:9656-9670 (2015).

(Continued)

*Primary Examiner* — Christopher R Tate
*Assistant Examiner* — Russell G Fiebig
(74) *Attorney, Agent, or Firm* — Rubin and Rudman, LLP

(57) ABSTRACT

The present invention provides a pharmaceutical or health functional food containing, as an active ingredient, a complex extract of *Crataegi Fructus* and *Citri Pericarpium*. The complex extract has the effects of reducing body weight and lipids in blood vessels.

4 Claims, 2 Drawing Sheets

(56) References Cited

OTHER PUBLICATIONS

Lim et al., "Anti-obesity effect of HT048, a herbal combination, in high fat diet-induced obese rats," Molecules 17:14765-14777 (2012).
Response to Communication Pursuant to Rules 161(2) and 162 EPC, submitted Oct. 23, 2015, in connection with European Application No. 13833473.5, 5 pages.
Extended European Search Report, dated Feb. 16, 2016, in connection with European Application No. 13833473.5, 8 pages.
Letter/Written Disclosure of the Supplemental Information Disclosure Statement for the above-referenced application, filed herewith on Mar. 3, 2017, 3 pages.
ChineseHerbsHealing.com, "Hawthorn Berry (Shan Zha)" [retrieved on Aug. 31, 2016 (online) from:URL:chineseherbshealing.com/hawthorn-berry/], 6 pages.
Royallivingformulas.com, "Pericarpium Citri Reticulatae (Chen Pi)," [retrieved on Aug. 31, 2016 (online) from:URL:royal-livingformulas.com/learn/tcm-ingredients/pericarpium-citri-reticulatae], 1 page.
Communication Pursuant to Article 94(3) EPC (Examination Report), dated Feb. 2, 2017, in connection with corresponding European Patent Application No. 13833473.5, 5 pages.
Letter/Written Disclosure of the Supplemental Information Disclosure Statement for the above-referenced application, filed herewith on Jan. 13, 2017, 2 pages.
Response filed Sep. 2, 2016, to Extended European Search Report, dated Feb. 16, 2016, in connection with European Patent Application No. 13833473.5, 16 pages.

\* cited by examiner

PHARMACEUTICAL COMPOSITION CONTAINING COMPLEX EXTRACT OF CRATAEGI FRUCTUS AND CITRI PERICARPIUM AS AN ACTIVE INGREDIENT FOR TREATING OR PREVENTING OBESITY OR LIPID-RELATED METABOLIC DISEASES

RELATED APPLICATIONS

This application is the U.S. National Stage of International Application. No. PCT/KR2013/005482, filed Jun. 21, 2013, which claims benefit of priority to Korean Patent Application No. KR 10-2012-0094213, filed Aug. 28, 2012, which is incorporated by reference herein.

TECHNICAL FIELD

The present invention relates to a pharmaceutical composition comprising a complex extract of *Crataegi Fructus* and *Citri Pericarpium* as an active ingredient for treating or preventing obesity or lipid-related metabolic diseases.

Moreover, the present invention relates to a health functional food comprising a complex extract of *Crataegi Fructus* and *Citri Pericarpium* as an active ingredient for ameliorating or preventing obesity or lipid-related metabolic diseases.

BACKGROUND ART

Obesity refers to a condition where excess fatty tissue is accumulated in the body by genetic, environmental, and psychological factors, which results in health disorders, and may cause serious health problems such as hypertension, hyperlipidemia, heart disease, diabetes, cancer, etc. all around the world. Accordingly, the World Health Organization (WHO) defined obesity as a disease in 1996 and recognizes obesity as a risk factor for major chronic diseases, and the Management of Obesity, 2010 Recommendation of the Korean Society for the Study of Obesity, states that obesity is a disease and must be treated.

The obese population is rapidly increasing all around the world, and the WHO reported that the obese population is 1.2 billion all around the world and will increase to 1.5 billion in 2015. Moreover, according to a report by the Organization for Economic Cooperation and Development (OECD), 31% of American population and 3.2% of Korean population are extremely obese with a BMI over 30 $kg/m^2$. Accordingly, the market for obesity drugs is rapidly growing and is expected to grow about 20% per year by 2014 based on 200 billion dollars in 2008.

However, the biggest problem in obesity treatment at present is drug abuse such as the use of unproven drugs or the abuse without the need for drug therapy. In particular, the use of antipsychotic obesity drugs should be limited to several weeks as adjuvant therapy for obesity, but is not carefully managed, resulting in a serious problem. Moreover, as the serious side effects of sibutramine, which acted as an appetite suppressant and accounted for about half of the market for obesity drugs in Korea, such as increased blood pressure, increased respiration, consciousness disorder, hypothyroidism, etc. were reported, sale of sibutramine was suspended in Europe and America in 2010, and then in Korea. Since then, the supply of phendimetrazine has increased, and thus the supply of obesity drugs is maintained at a ordinary level, but the side effects occurring during administration still remain as a serious problem.

Weight control methods for the treatment of obesity include dietary therapy, exercise therapy, behavior modification therapy, etc. in addition to the drug therapy, and the diet-related industry covers a variety of fields such as delicatessen for weight control, diet health functional foods, fitness centers, obesity clinics, etc. In particular, the Korean market for diet foods is about 150 to 200 billion Korean won and is growing annually by 7 to 10%. As the serious side effects of obesity drugs have become known to the public, much interest is focused on herb medicines that are easier to access and have fewer side effects than the obesity drugs.

Among the representative health functional foods for control weight, conjugated linoleic acids (CLA) are conjugated double bond isomers of linoleic acid, and their effects such as reduced fat absorption and suppressed fat accumulation due to inhibited lipoprotein lipase, increased basal metabolic rate (BMR) due to increased mitochondrial activity, reduced fat cells due to increased apoptosis of fat cells, etc. were reported in several experiments. Moreover, it was reported in clinical trials that when a person took about 3 g of conjugated linoleic acid on a daily basis, an average of 2.5 kg of body weight was lost after 3 months, and 15 to 20% of body fat was reduced. However, it was reported that the weight loss effects did not appear to be consistent, might increase insulin resistance, and might induce fatty liver. Therefore, there is a need for attention to the administration of conjugated linoleic acid products to patients with increased insulin resistance including type II diabetic patients.

*Garcinia cambogia*, another health functional food for weight control, is a plant of *garcinia* species originated from India, and it is known that about 10 to 30% hydroxycitrate (HCA) contained in the fruit peels of *garcinia cambogia*, which inhibits the action of ATP-citrate lyase, and thus inhibits the fatty acid biosynthesis and reduces the intake of fats, resulting in suppressed body weight gain. As a result of applying *cambogia* extracts to clinical trials based on the HCA intake, the weight loss effects due to reduced body fat, increased excretion of fat metabolites, reduced energy intake, etc. were reported, but these are short-term results obtained for a period of 10 days to 12 weeks, and a 12-week clinical trial showed that the group given a dose of 1,500 mg HCA daily had no weight loss effect, compared to the placebo group. Furthermore, there are no results of a long-term research on HCA, and thus it is difficult to make a decision on the weight loss effects.

With respect to effect, there are no health functional foods taken for the treatment of obesity, which are more effective than the drugs prescribed for the treatment of obesity at present. Moreover, due to large variations in prices between products and due to false advertisement for functionalities, consumers are confused about the selection of products, and their prices are not so low in terms of their therapeutic effects. Even some foods that are known to be effective for the weight loss can get the weight loss effects only when combined with regular exercise and diet. However, the market for products with unproven efficacy is highly concentrated due to vague expectations of the efficacy of foods, and thus there is an urgent need for the development of naturally occurring foods for which efficacy can be objectively proven.

*Crataegi Fructus* is a dried fruit of *Crataegus pinnatifida*, a deciduous tree belonging to the family Rosaceae, and is a medical herb that has been widely used in Oriental medicine for a long time, which acts on the spleen, stomach, and liver to remove indigestion, promote food digestion, and remove extravasated blood. The principal ingredients of *crataegi*

*fructus* include organic acids, such crataegolic acid, citric acid, succinic acid, chlorogenic acid, caffeic acid, and oleanolic acid, and flavonoid compounds such as quercetin, vitexin, epicatechin, and rutin, and these ingredients exhibit effects on digestive organs, hypotensive effects, antibacterial effects, cardiotonic effects, etc. At present, it is reported that an extract of *crataegi fructus* has antioxidant effects, blood lipid inhibitory effects, etc. and exhibits weight loss effects in animal experiments.

*Citri Pericarpium* is a dried peel of mature fruit of citrus unshiu, an evergreen small tree belonging to the family Rutaceae, and is a medical herb that has been widely used in Oriental medicine for a long time, which acts mainly on the spleen to promote digestion and remove abdominal pain due to indigestion. The principal ingredients of *Citri Pericarpium* contain limonene, α, β-pinene, etc. and flavonoid compounds such as hesperidin (about 8.4%), neohesperidin, tangeritin, citromitin, 5-O-desmethyl citromitin, etc. These ingredients exhibit the effects of gastrointestinal smooth muscle relaxation, increased secretion of gastric juice, anti-stomach ulcer, anti-inflammation, etc., and it is reported that an extract of *Citri Pericarpium* has blood lipid inhibitory effects, weight loss effects, adipogenesis inhibitory effects, etc.

Accordingly, the present inventors have found that HT048, a composition comprising *Crataegi Fructus* and *Citri Pericarpium*, is useful for blood lipid reduction and weight loss more effectively than individual drugs, and completed the present invention.

DISCLOSURE

Technical Problem

An object of the present invention is to provide a pharmaceutical composition comprising a complex extract of *Crataegi Fructus* and *Citri Pericarpium* as an active ingredient for treating or preventing obesity or lipid-related metabolic diseases.

Another object of the present invention is to provide a health functional food comprising a complex extract of *Crataegi Fructus* and *Citri Pericarpium* as an active ingredient for ameliorating or preventing obesity or lipid-related metabolic diseases.

Technical Solution

One embodiment of the present invention provides a pharmaceutical composition comprising a complex extract of *Crataegi Fructus* and *Citri Pericarpium* as an active ingredient for treating or preventing obesity or lipid-related metabolic diseases.

The lipid-related metabolic diseases may be selected from the group consisting of diabetes, hyperlipidemia, hypertension, arteriosclerosis, fatty liver, stroke, and cardiovascular disease.

The weight ratio of *Crataegi Fructus* and *Citri Pericarpium* contained in the complex extract may preferably be 7:1 to 1:7, more preferably 2:1 to 1:2.

Moreover, the complex extract may be extracted from water, C1-C4 alcohol, or a mixture thereof, and the C1-C4 alcohol may preferably be methanol or ethanol.

Another embodiment of the present invention provides a health functional food comprising a complex extract of *Crataegi Fructus* and *Citri Pericarpium* as an active ingredient for ameliorating or preventing obesity or lipid-related metabolic diseases.

The weight ratio of *Crataegi Fructus* and *Citri Pericarpium* contained in the complex extract and the extraction solvent are the same as those described in the pharmaceutical composition, and the health functional food may preferably be a health functional beverage.

Advantageous Effects

The composition comprising a complex extract of *Crataegi Fructus* and *Citri Pericarpium* as an active ingredient of the present invention has the effects of reducing body weight and blood lipids, and thus can be used for treating or preventing obesity or lipid-related metabolic diseases.

BEST MODE FOR CARRYING OUT THE INVENTION

Hereinafter, the present invention will be described in detail.

The present invention provides a composition comprising a complex extract of *Crataegi Fructus* and *Citri Pericarpium* as an active ingredient.

Method of Preparing Complex Extract of *Crataegi Fructus* and *Citri Pericarpium*

The complex extract of the present invention is preferably prepared by a method comprising the following steps, but not limited thereto:

(1) drying and crushing *Crataegi Fructus* and *Citri Pericarpium*;

(2) extracting an extract by adding an extraction solvent to the crushed *Crataegi Fructus* and *Citri Pericarpium*;

(3) cooling and filtering the extract; and (4) concentrating the filtered extract under reduced pressure and drying the concentrated extract.

The *Crataegi Fructus* and *Citri Pericarpium* used in step (1) may be those grown or commercially available without any limitation.

The extraction in step (2) may be performed by shaking extraction, Soxhlet extraction or reflux extraction, but not limited thereto. The extraction temperature may preferably be 40 to 100° C., more preferably 60 to 80° C. Moreover, the extraction time may preferably be 2 to 24 hours, and the number of extractions may preferably be 1 to 5 times, more preferably more than 2 times.

The extraction solvent used in step (2) may be water, alcohol, or a mixture thereof. The alcohol may preferably be C1-C4 lower alcohol, more preferably methanol or ethanol. The concentration of the alcohol may preferably be 0 to 100%, more preferably 30%. Moreover, the extraction may preferably be performed by adding the extraction solvent in a weight or volume of 5 to 15 times the *Crataegi Fructus* and *Citri Pericarpium* prepared in step (1), more preferably 10 times.

The concentration under reduced pressure in step (4) may preferably be performed using a vacuum reduced-pressure concentrator or vacuum rotary evaporator, and the drying may preferably be performed by drying under reduced-pressure, vacuum drying, boiling drying, spray drying, or freeze drying, but not limited thereto.

Pharmaceutical Composition

The present invention provides a pharmaceutical composition comprising a complex extract of *Crataegi Fructus* and *Citri Pericarpium* as an active ingredient for treating or preventing obesity.

Figure 1:
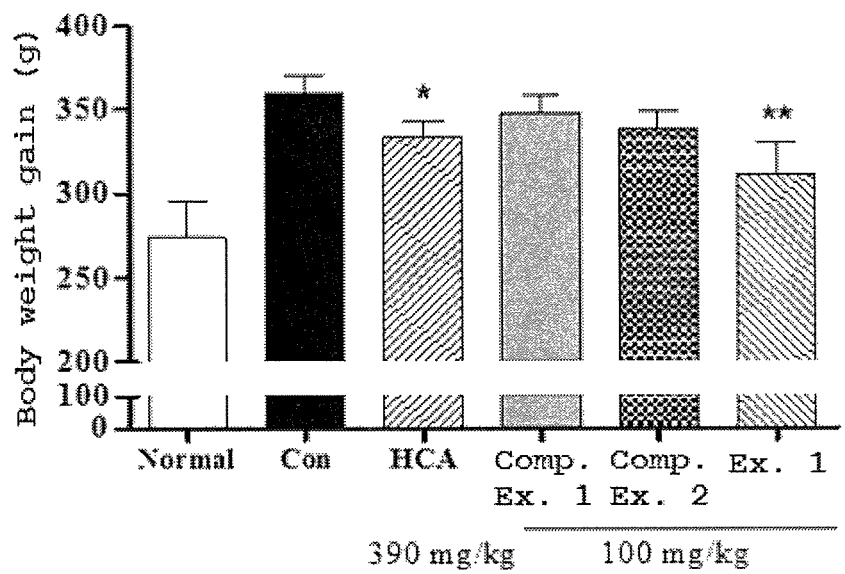
FIG. 1 is a diagram showing the change in weight of high-fat diet obese animal models.

The pharmaceutical composition has the effect of minimizing body weight gain even in an obese environment due to high-fat diet, which can be seen from FIG. 1. Accordingly, the pharmaceutical composition of the present invention can be used to control an obese patient's weight to be close to a normal weight or prevent a normal person from being an obese patient.

Moreover, the present invention provides a pharmaceutical composition comprising a complex extract of *Crataegi Fructus* and *Citri Pericarpium* as an active ingredient for treating or preventing lipid-related metabolic diseases.

The lipid-related metabolic diseases may be at least one disease selected from the group consisting of diabetes, hyperlipidemia, hypertension, arteriosclerosis, fatty liver, stroke, and cardiovascular disease.

Figure 2:
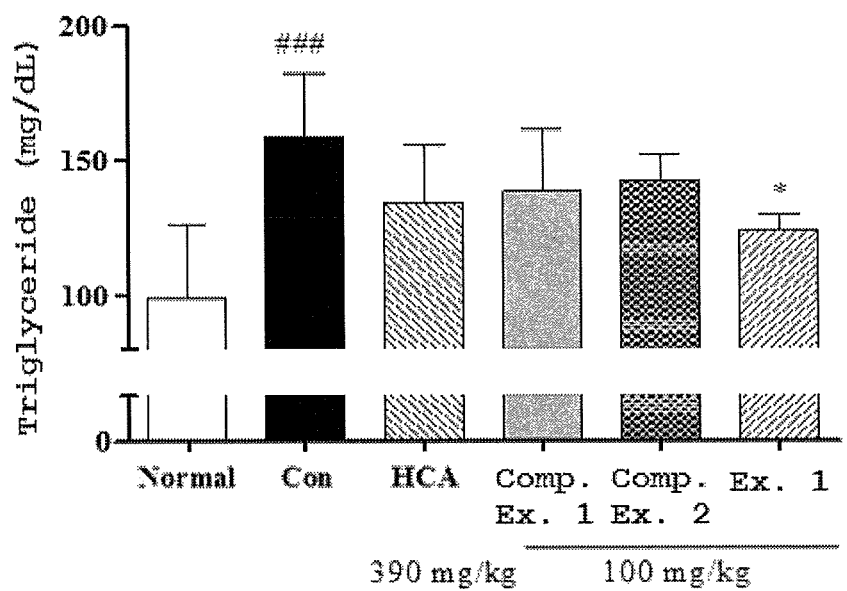
FIG. 2 is a diagram showing the change in concentration of blood triglyceride in high-fat diet obese animal models.
Figure 3:
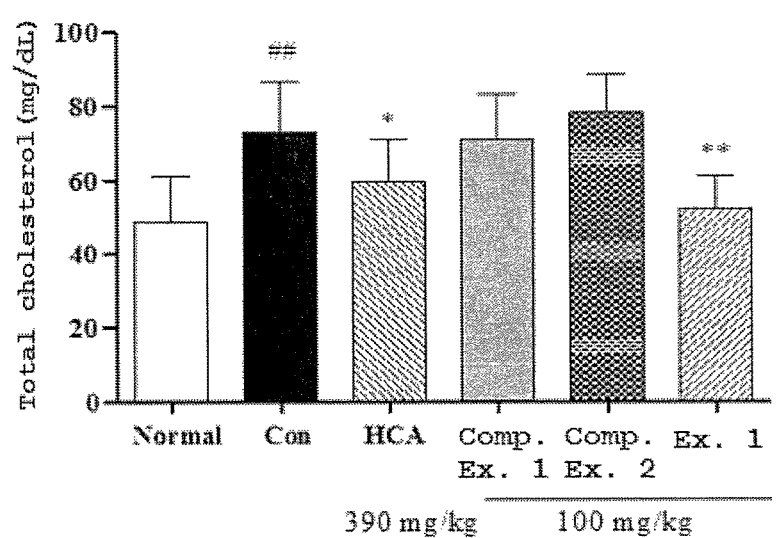
FIG. 3 is a diagram showing the change in concentration of blood total cholesterol in high-fat diet obese animal models.

The pharmaceutical composition has the effects of reducing the concentration of blood triglyceride and the concentration of blood total cholesterol, which can be seen from FIGS. 2 and 3. Accordingly, the pharmaceutical composition of the present invention can be used to treat or prevent lipid-related metabolic diseases.

The complex extract of *Crataegi Fructus* and *Citri Pericarpium* in the pharmaceutical composition as an active ingredient of the present invention may preferably be contained in an amount of 0.1 to 50 wt % with respect to the total weight of the composition.

The pharmaceutical composition of the present invention may be administered in various dosage forms such as oral and parenteral dosage forms during actual clinical administration. For formulation, the pharmaceutical composition can be formulated with generally used diluents or excipients such as fillers, extenders, binders, wetting agents, disintegrating agents, surfactants, etc.

Solid dosage forms for oral administration may include tablets, pills, powders, granules, and capsules, and these solid dosage forms are prescribed by mixing at least one excipient such as starch, calcium carbonate, sucrose, lactose, and gelatin. Moreover, lubricants such as magnesium stearate, talc, etc. can be used in addition to simple excipients.

Liquid dosage forms for oral administration may include suspensions, liquids for internal use, emulsions, and syrups, and various excipients such as wetting agents, sweeteners, flavoring agents, preservatives, etc. can be used in addition to generally used simple diluents such as water, liquid paraffin, etc.

Dosage forms for parenteral administration may include sterilized aqueous solutions, non-aqueous solvents, suspensions, emulsions, freeze-dried preparations, and suppositories. Examples of the non-aqueous solvents and suspensions may include vegetable oils such as propylene glycol, polyethylene glycol, and olive oil and injectable esters such as ethyl oleate. Examples of suppository bases may include Witepsol, macrogol, Tween 61, cocoa butter, laurin butter, glycerol, gelatin, etc. For parenteral administration, the pharmaceutical composition of the present invention can be administered via subcutaneous injection, intravenous injection, or intramuscular injection.

The dose of the pharmaceutical composition may vary depending on a patient's state and weight, the severity of disease, the form of drug, and administration route and duration and can be appropriately selected by those skilled in the art. However, for a desired effect, the pharmaceutical composition of the present invention may preferably be administered at a dose of 0.0001 to 100 mg/kg per day. The daily dose may be administered once a day or in equally divided doses. However, the dose does not limit the scope of the present invention.

Health Functional Food

The present invention provides a health functional food comprising a complex extract of *Crataegi Fructus* and *Citri Pericarpium* as an active ingredient for ameliorating or preventing obesity.

The health functional food has the effect of controlling an obese patient's weight to be close to a normal weight or preventing a normal person from being an obese patient.

Moreover, the present invention provides a health functional food comprising a complex extract of *Crataegi Fructus* and *Citri Pericarpium* as an active ingredient for ameliorating or preventing lipid-related metabolic diseases.

The health functional food has the effect of reducing the lipid concentration and thus ameliorating or preventing lipid-related metabolic diseases.

The health functional food of the present invention may comprise the complex extract of the present invention as it is or can be used in combination with other foods or food ingredients and can be appropriately used according to a conventional method.

The content of the active ingredient in the health functional food can be determined appropriately depending on the purpose of use (prevention, healthy or therapeutic treatment). In general, during the production of food or beverage, the complex extract of the present invention may be added in an amount of 0.01 to 15 wt % with respect to the total weight of the food.

The type of the health functional food is not particularly limited. Example of the health functional food to which the complex extract of the present invention can be added may include beverages, gums, vitamin complexes, health drinks, etc. and may encompass all health functions foods in a general sense.

The health functional food of the present invention may comprise various nutrients, vitamins, minerals (electrolytes), flavors such as synthetic flavors and natural flavors, colorants and enhancers (cheeses, chocolates, etc.), pectic acid and its salts, alginic acid and its salts, organic acid, protective colloidal thickeners, pH adjusting agents, stabilizers, preservatives, glycerin, alcohol, carbonizing agents used in carbonated drinks, etc.

MODE FOR INVENTION

Examples

Next, preferred Examples will be provided to facilitate understanding of the present invention. However, the following Examples are provided for better understanding of the present invention, and the scope of the present invention is not limited by the Examples.

Example 1: Preparation of Complex Extract

*Crataegi Fructus* and *Citri Pericarpium* were purchased from Yaksudang (Dongdaemun-gu, Seoul). 30% ethanol was added to 62.5 g of *Crataegi Fructus* and 37.5 g of *Citri Pericarpium* in a weight of 10 times the total weight of each ingredient and extracted at 80° C. for 3 hours twice. Filtrates of the extracts were concentrated under reduced pressure to 60 Brix, freeze-dried in the form of power, and then mixed.

Example 2: Preparation of Complex Extract

Extract was prepared and mixed by the same method as Example 1, except that 50 g of *Crataegi Fructus* and 50 g of *Citri Pericarpium* were used.

The contents of *Crataegi Fructus* and *Citri Pericarpium* contained in the complex extracts of Examples 1 and 2 are shown in the following Table 1:

TABLE 1

|           |              | Crataegi Fructus | Citri Pericarpium |
|-----------|--------------|------------------|-------------------|
| Example 1 | Weight (g)   | 62.5             | 37.5              |
|           | Weight ratio | 5                | 3                 |
| Example 2 | Weight (g)   | 50               | 50                |
|           | Weight ratio | 1                | 1                 |

Comparative Example 1: Preparation of *Crataegi Fructus* Extract

Extract was prepared by the same method as Example 1, except that 100 g of *Crataegi Fructus* was used.

Comparative Example 1: Preparation of *Citri Pericarpium* Extract

Extract was prepared by the same method as Example 1, except that 100 g of *Citri Pericarpium* was used.

The contents of *Crataegi Fructus* and *Citri Pericarpium* contained in the extracts of Comparative Examples 1 and 2 are shown in the following Table 2:

TABLE 2

|                       |              | Crataegi Fructus | Citri Pericarpium |
|-----------------------|--------------|------------------|-------------------|
| Comparative Example 1 | Weight (g)   | 100              | 0                 |
|                       | Weight ratio | 1                | 0                 |
| Comparative Example 2 | Weight (g)   | 0                | 100               |
|                       | Weight ratio | 0                | 1                 |

Example 3: Determination of Effects of Complex Extract on Weight Loss and Lipid Reduction 1. Overview of Experiments Animal models, diet-induced obesity (DIO) white rat models, which exhibit a similar process to the case where a person becomes obese, were used.

2. Experimental Animals

Animal experiments were performed on Sprague-Dawley (SAMTAKO BIO Korea) male white rats weighing 80 to 100 g.

3. Selection of Experimental Groups

Normal group (AIN-93G, Normal diet+fed with secondary distilled water);
Control group (60% Kcal high-fat diet+fed with secondary distilled water);
Positive control group (60% Kcal high-fat diet+administered with 390 mg/kg of HCA);
*Crataegi Fructus* extract-administered group (high-fat diet+administered with 100 mg/kg of the*Crataegi Fructus* extract of Comparative Example 1);
*Citri Pericarpium* extract-administered group (high-fat diet+administered with 100 mg/kg of the *Citri Pericarpium* extract of Comparative Example 2); and
Complex extract-administered group (high-fat diet+administered with 100 mg/kg of the complex extract of Example 1 or 2).

4. Experimental Conditions

The temperature was 22±2° C., the relative humidity was 50±10%, and the dark-light cycle (light on at 07:00~light off at 19:00) was controlled with fluorescent lighting.

All the experimental groups were orally administered twice a day for 8 weeks, and during the experiments, the measurement of weight was performed once a day, and the measurement of feed intake was performed every three days. Moreover, all the experimental groups were sacrificed after 8 weeks to collect blood samples, serums were separated from the blood samples, and the blood triglyceride (mg/dL) and the total cholesterol (mg/dL) were analyzed using a biochemical analyzer (VetTest 8008, IDEXX, USA).

5. Experimental Results

After administration to each group for 8 weeks, the reduction in the rate of body weight gain (g) in the groups administered with 100 mg/kg of the *Crataegi Fructus* extract and the *Citri Pericarpium* extract, respectively, was 3.2% and 5.7%, which were statistically insignificant compared to the control group.

However, the reduction in the rate of body weight gain (g) in the group administered with 100 mg/kg of the complex extract was significantly reduced by 13% (359.3±10.5 g VS 311.5±18.5 g, P<0.01) (mean±SD), which was higher than the positive control group administered with 390 mg/kg of HCA (see FIG. 1).

Moreover, after all the experimental groups were sacrificed after 8 weeks to collect blood samples and the serums separated from the blood samples were analyzed, the concentration of blood triglyceride (mg/dL) in the groups administered with 100 mg/kg of the *Crataegi Fructus* extract and the *Citri Pericarpium* extract, respectively, was reduced by 12.7% and 10%, which, however, were statistically insignificant compared to the control group.

However, the concentration of blood triglyceride (mg/dL) in the group administered with 100 mg/kg of the complex extract was significantly reduced by 21.7% (158.4±23.9 mg/dL VS 124±5.8 mg/dL, P<0.05), which was higher than the control group (see FIG. 2).

Moreover, the concentration of blood total cholesterol (mg/dL) in the group administered with 100 mg/kg of the *Crataegi Fructus* extract was reduced by 2.5% compared to the control group, but the group administered with 100 mg/kg of the *Citri Pericarpium* extract showed no reduction in the total cholesterol concentration.

However, the concentration of blood total cholesterol in the group administered with 100 mg/kg of the complex extract was reduced by 28.4%, which was significantly higher than the control group (72.9±13.6 mg/dL VS 52.2±8.7 mg/dL, P<0.01) (see FIG. 3).

The above experimental results are summarized in the following Tables 3 and 4:

TABLE 3

|                         | Body weight gain (g) | Reduction in rate of body weight gain (%) |
|-------------------------|----------------------|-------------------------------------------|
| Negative control (Saline) | 359.3 ± 16.6       | —                                         |
| Positive control (HCA)    | 333.2 ± 12.2*      | 7.3*                                      |

TABLE 3-continued

|  | Body weight gain (g) | Reduction in rate of body weight gain (%) |
|---|---|---|
| Comparative Example 1 | 347.7 ± 10.8 | 3.2 |
| Comparative Example 2 | 338.7 ± 20.5 | 5.7 |
| Example 1 | 311.5 ± 15.2** | 13.3** |
| Example 2 | 312.6 ± 9.1* | 13* |

TABLE 4

|  | Total triglyceride (mg/dL) | Total cholesterol (mg/dL) |
|---|---|---|
| Negative control (Saline) | 158.4 ± 23.9 | 72.9 ± 13.6 |
| Positive control (HCA) | 134.2 ± 21.3 | 59.8 ± 11.2* |
| Comparative Example 1 | 138.3 ± 23.5 | 71.1 ± 12.1 |
| Comparative Example 2 | 142.5 ± 9.2 | 78.2 ± 10.3 |
| Example 1 | 124 ± 5.8* | 52.2 ± 8.7** |
| Example 2 | 126.7 ± 19.1* | 52.6 ± 9.7** |

(*$P < 0.05$,
**$P < 0.01$)

Formulation Example 1: Preparation of Tablets

| The complex extract of Example 1 | 200 mg |
|---|---|
| Lactose | 100 mg |
| Starch | 100 mg |
| Magnesium stearate | q.s |

The above ingredients were mixed and compressed to prepare tablets according to a conventional tablet preparation method.

Formulation Example 2: Preparation of Capsules

| The complex extract of Example 1 | 200 mg |
|---|---|
| Lactose | 50 mg |
| Starch | 50 mg |
| Talc | 2 mg |
| Magnesium stearate | q.s |

The above ingredients were mixed and filled into gelatin capsules to prepare capsules according to a conventional capsule preparation method.

Formulation Example 3: Preparation of Liquids

| The complex extract of Example 1 | 1,000 mg |
|---|---|
| Sugar | 20 g |
| Isomerized glucose syrup | 20 g |
| Lemon flavor | q.s |

Purified water was added to make a total of 1,000 mL. The above ingredients were mixed, filled into brown bottles, and sterilized to prepare liquids according to a conventional liquid preparation method.

The above ratio illustrates a preferred example of mixing ingredients relatively suitable for a beverage, but it can be arbitrarily changed according to regional and national preferences such as demand classes, demand nations, uses, etc.

Formulation Example 4: Preparation of Health Functional Food

| The complex extract of Example 1 | 1,000 mg |
|---|---|
| Vitamin mixture | q.s |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Nicotinic acid amide | 1.7 mg |
| Folic acid | 50 μg |
| Calcium pantothenate | 0.5 mg |
| Mineral mixture | q.s |
| Ferrous sulfate | 1.75 mg |
| Zinc oxide | 0.82 mg |
| Magnesium carbonate | 25.3 mg |
| Potassium monophosphate | 15 mg |
| Potassium diphosphate | 55 mg |
| Potassium citrate | 90 mg |
| Calcium carbonate | 100 mg |
| Magnesium chloride | 24.8 mg |

The above ratio of vitamins and minerals illustrates a preferred example of mixing ingredients relatively suitable for a health functional food, but it can be arbitrarily changed. According to a conventional health functional food preparation method, the above ingredients are mixed and used for preparation of a health functional food composition by a conventional method (e.g., nutrient candies).

Formulation Example 5: Preparation of Health Functional Beverage

| The complex extract of Example 1 | 1,000 mg |
|---|---|
| Citric acid | 1,000 mg |
| Oligosaccharide | 100 g |
| Plum extract | 2 g |
| Taurine | 1 g |
| Total with purified water added | 900 mL |

According to a conventional health functional beverage preparation method, the above ingredients were mixed, stirred and heated at 85° C. for about 1 hour, and the prepared solution was filtered, filled into 2 L sterile bottles, sealed, sterilized, and kept under refrigeration, and then used for preparation of a health functional beverage composition.

The above ratio illustrates a preferred example of mixing ingredients relatively suitable for a beverage, but it can be arbitrarily changed according to regional and national preferences such as demand classes, demand nations, uses, etc.

INDUSTRIAL APPLICABILITY

As described above, the present invention can provide a composition for treating or preventing obesity or lipid-related metabolic diseases.

The invention claimed is:

1. A pharmaceutical composition for reducing the concentration of blood triglycerides or blood total cholesterol and/or for reducing body weight comprising an effective amount of a complex extract,
  wherein the complex extract is a synergistic combination of extracts obtained by extraction of *Crataegi Fructus* and *Citri Pericarpium* with ethanol, wherein the ratio of *Crataegi Fructus* and *Citri Pericarpium* is 5:3 or 1:1, and wherein the composition is in the form of a tablet, a pill, or a capsule.

2. The pharmaceutical composition of claim 1, wherein the complex extract is present in an amount of 0.1 to 50 wt % with respect to the total weight of the composition.

3. A method for reducing the concentration of blood triglyceride or blood total cholesterol in a subject in need thereof, comprising administering an effective amount of the pharmaceutical composition of claim 1 to said subject.

4. A method for reducing body weight in a subject in need thereof, comprising administering an effective amount of the pharmaceutical composition of claim 1 to said subject.

\* \* \* \* \*